United States Patent [19]

Mesek

[11] 4,285,342
[45] Aug. 25, 1981

[54] DISPOSABLE DIAPER

[75] Inventor: Frederick K. Mesek, Tinley Park, Ill.

[73] Assignee: Johnson & Johnson Baby Products Company, New Brunswick, N.J.

[21] Appl. No.: 45,030

[22] Filed: Jun. 4, 1979

[51] Int. Cl.³ .................................. A41B 13/02
[52] U.S. Cl. ................................................ 128/287
[58] Field of Search ................... 128/284, 286, 287

[56] References Cited

U.S. PATENT DOCUMENTS

| 2,581,904 | 1/1952 | Burns | 128/287 |
|---|---|---|---|
| 2,817,338 | 12/1957 | Slusser | 128/286 |
| 3,103,930 | 9/1963 | Collett et al. | 128/286 |
| 3,344,789 | 10/1967 | Arnold et al. | 128/287 |
| 3,386,442 | 6/1968 | Sabee | 128/287 |
| 3,441,023 | 4/1969 | Rijssenbeek | 128/287 |
| 3,665,920 | 5/1972 | Davis | 128/287 |
| 3,837,343 | 9/1974 | Mesek | 128/284 |
| 3,844,288 | 10/1974 | Kiela | 128/287 |
| 3,965,906 | 6/1976 | Karami | 128/287 |
| 4,069,822 | 1/1978 | Buell | 128/284 |

Primary Examiner—C. Fred Rosenbaum
Attorney, Agent, or Firm—Martha A. Michaels

[57] ABSTRACT

The invention provides an absorbent structure, such as a disposable diaper or a training panty, including a first outer layer in the form of a moisture-impervious backing sheet, a second outer layer in the form of a liquid barrier positioned in superposed relationship with respect to the backing sheet and an absorbent batt sandwiched between the first and second outer layers. The liquid barrier has a single opening situated so as to contact the perineal region of the wearer.

8 Claims, 8 Drawing Figures

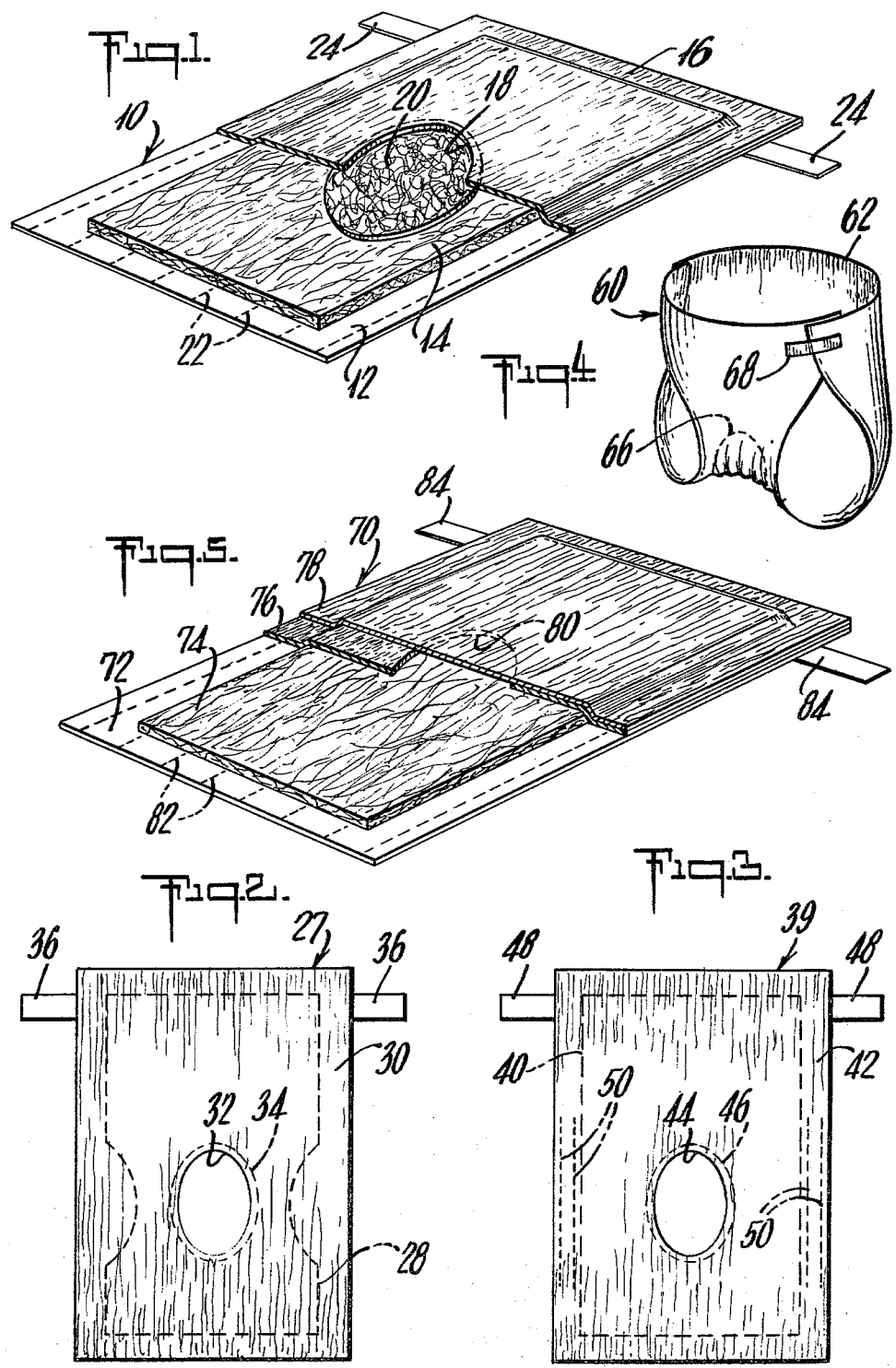

DISPOSABLE DIAPER

BACKGROUND OF THE INVENTION

Disposable diapers have met with increased commercial acceptance in recent years primarily because of their convenience, as opposed to cloth diapers, which need to be laundered once soiled. Many different constructions have been proposed and used, and some have met with widespread commercial success in spite of certain inadequacies in functional properties.

One of the most serious prior art problems has been the inability to provide a suitable construction that would keep moisture away from the surface of the diaper which comes into contact with the infant's skin and thereby avoids skin irritation and infection. Commonly assigned Mesek et al U.S. Pat. No. 3,612,055 discloses several diaper constructions that function very well in keeping moisture away from an infant's skin, while at the same time handling a full volume discharge of urine.

These functions are accomplished by a multilayer diaper comprising, in order, a fibrous facing layer which is to be brought into contact with the infant's skin, a layer of a highly porous, loosely compacted cellulosic batt, a paper-like densified, highly compacted cellulosic fibrous layer integral with the loosely compacted batt, and a moisture-impervious backing sheet adhered to the densified layer at the interface therebetween. The facing layer is of porous construction and its fibers have less wettability for water than the fibers of the loosely compacted batt, resulting in a tendency for liquid to flow from the facing layer into the batt. The densified fibrous layer has a smaller average pore size than the loosely compacted batt, resulting in a tendency for liquid to flow preferentially from the batt into the underlying densified layer rather than to other areas of the batt, thus tending to restrict wetting in the batt to an area of moderate size. Liquid flowing into the densified layer tends to spread laterally because of its wicking action and liquid which might pass through the densified layer during discharge (when flow is rapid) is held back by the impervious backing sheet for sufficient time to permit absorption to take place. Liquid in excess of the absorptive capacity of the densified layer is forced back by the impervious layer into the dry portion of the loosely compacted batt, thus utilizing the additional absorptive capacity therein.

While the diaper structure described in the above-mentioned patent represents a significant advance in the art, particularly in its ability to maintain the layer in contact with an infant's skin dry, during periods of heavy discharge, after the densified layer and integral loosely compacted batt becomes saturated, there is a tendency for urine to wick back into the facing layer.

Also there exists a need for a disposable training panty which can be used during the transition period between diapers and reusable undergarments. An undergarment of this general type would also be useful with incontinent adults and children because of their absorbent properties, fit, and disposability.

Currently available training pants are generally made from knitted or woven cloth, such as cotton, or cotton-polyester blends. They may or may not include additional absorbent layers in the crotch area and they may include a water-repellent outer layer.

The prior art and commercially available training pants suffer from a number of disadvantages, however. Aside from the obvious disadvantage of having to be laundered, the primary disadvantage of the currently available conventional cloth training panty is the problem of liquid strike-through. The prior art has attempted to solve this problem by providing areas of extra absorbency utilizing, for example, terrycloth or a piled fabric in the crotch portion of the panty and/or additionally including a water-repellent outer layer in the crotch area, or over the entire outer surface of the panty. However, as anyone knows who has ventured through the traumatic training period with their babies, the prior art simply has not provided a satisfactory solution.

For the above reasons, many mothers continue to use diapers during the training period, rather than suffer the annoyance of liquid strike-through when their child has an accident. While the use of diapers substantially reduces the problem of liquid strike-through diaper use during the training period is highly undesirable and tends to prolong the period required to completely train the child. Psychologically, it is desirable for children to be in panties during the training period so they are aware of no longer being babies and are more aware of accidents.

Aside from the undesirable psychological drawbacks of continuing to use diapers during the training period, disposable diapers present an economic drawback. Disposable diapers generally utilize tape tab fasteners in place of safety pins as fastening means. When the tabs are removed so that the child can be placed on the toilet, the unsoiled diaper must be discarded because the currently available tabs are for a single use only and usually tear the backing fabric when they are pulled away.

A variety of disposable panties are known. See, for example, U.S. Pat. Nos. 3,424,162; 3,599,638; 3,599,640; and 3,636,953. Such panties are provided with or adapted to receive a sanitary napkin in the crotch portion of the panty and are not adapted to deal with the liquid strike-through problem encountered during the training period or with incontinent adults or children. Similarly, the disposable panty types disclosed in U.S. Pat. Nos. 3,663,962; 3,245,407 and 3,488,778, do not satisfy the need for a disposable training panty, because the panties are either nonabsorbent, such as plastic, or lack the necessary fit in the leg and waist area to prevent the problem of liquid strike-through and leakage.

In accordance with co-pending application U.S. Ser. No. 898,374, filed Apr. 20, 1978, a disposable undergarment is provided which is used as a training panty during the training period. The undergarment is constructed of one or more plies of stretchable non-woven fabric. Preferably, several plies of stretchable, non-woven fabric are utilized to provide different absorption and moisture-permeability characteristics for the inner and the outer layer of the undergarment, as well as good conformability and fit without attendant bulkiness. The inner, or facing, layer of the undergarment provides an innermost ply having a soft surface for contact with the wearer's skin, readily permits passage of excreted body liquids therethrough, and can provide an absorbent mass for body liquids as well, if desired. The outer, or backing, layer of the undergarment, on the other hand, presents at least one ply which is an effective liquid barrier and which prevents or substantially minimizes body liquid strike-through. The non-woven outer fabric layer, as well as the non-woven inner fabric layer, are micropleated in the machine direction of the fabric and compacted in the cross-direction of the fabric to give enhanced stretch or extensibility characteristics.

A preferred disposable undergarment comprises two stretchable, non-woven fabric layers having one or more plies each, preferably compressively-shrunk non-woven fabrics, and an absorbent layer or panel which is disposed between the inner and outer layers at least in the crotch portion of the undergarment. If desired, the absorbent layer can extend further up the back and/or the front portions of the undergarment. The undergarment has a self-fitting waist aperture and self-fitting leg apertures.

Further description of the training panty appears in the aforementioned co-pending application which is incorporated herewith by reference.

The absorbent structure disclosed herein represents an improvement over the absorbent structures disclosed in the above-mentioned patent and co-pending application by providing a liquid barrier between the absorbent batt and the infant's skin to prevent the urine from flowing back and wetting the infant's skin.

SUMMARY OF THE INVENTION

To achieve this important result, the absorbent structure of the present invention includes a first outer layer in the form of a moisture-impervious backing sheet; an absorbent batt positioned in superposed relationship with respect to the backing sheet, the batt being smaller than the backing sheet and spaced inwardly from the longitudinal sides thereof; and a second outer layer in the form of a liquid barrier positioned in superposed relationship with respect to the batt on the side opposite the backing sheet, the liquid barrier being larger than the batt and having longitudinal side margins thereof secured to the backing sheet, and having a single opening in the liquid barrier situated so as to contact the perinal region of the wearer.

In a preferred embodiment the absorbent batt includes a paper-like, densified compacted cellulosic fibrous layer of relatively high wettability and relatively high fluid retentivity integral with the batt on the side thereof in contact with the backing sheet.

The densified skin portion provides a wickability gradient to draw urine from the more loosely compacted cellulosic fibrous layer into the densified layer. When the densified skin portion becomes saturated, the excess urine flows back but is prevented from contacting the infant's skin by the liquid barrier placed on the opposite side of the absorbent batt toward the infant's skin.

BRIEF DESCRIPTION OF THE DRAWINGS

Briefly the drawings may be described as follows:

FIG. 1 is a perspective view, with certain portions broken away for clarity of illustration, of an open unfolded diaper of the present invention;

FIG. 2 is a top view illustrating the particular configuration of one embodiment of an absorbent batt in accordance with the present invention;

FIG. 3 is a top view illustrating the particular configuration of another embodiment of the diaper of the present invention;

FIG. 4 is a perspective view on a reduced scale of a diaper of the present invention in its configuration after being put on an infant;

FIG. 5 is a perspective view, with certain portions broken away for clarity of illustration, of one embodiment of a diaper of the present invention;

DETAILED DESCRIPTION OF THE INVENTION

Figure 6:
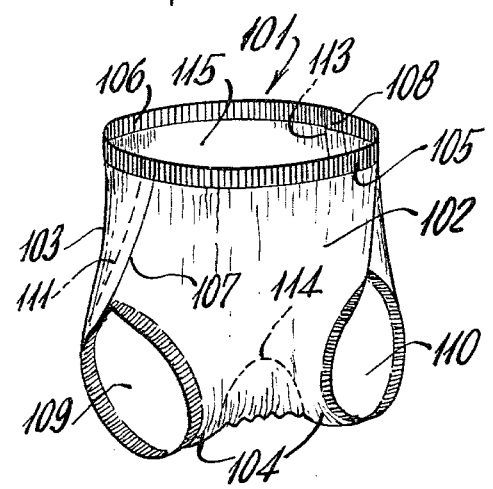
FIG. 6 is a perspective view of a disposable training panty embodying this invention.

Referring to the drawings, and particularly to FIG. 1, the diaper assembly 10 when fully open and laid out flat, comprises a lowermost moisture-impervious sheet 12 which is rectangular in shape, a highly liquid-absorbent fibrous batt, or panel 14, which is also rectangular in shape, but smaller than the impervious sheet 12 and centrally disposed thereon, and an overlying liquid barrier 16 of moisture-repellent material, which is also rectangular in shape, equal to dimension, and coterminous with the impervious sheet 12 and in contact therewith in the marginal portions of the diaper extending peripherally beyond the absorbent batt.

The liquid barrier 16 includes an opening 18 situated so as to contact the perineal region of the wearer. Immediately below the opening can be seen a covering 20 for the opening comprised of a water-wettable bonded web of mixed short and long fibers. The covering readily accepts liquid permitting the urine to penetrate through to the absorbent batt while simultaneously preventing wadding and/or linting of the fibers of the absorbent batt below.

Glue lines 22 adhere the impervious sheet 12 to the absorbent batt 14 thus lending integrity to the absorbent batt. Adhesive tabs 24 are affixed to the backing sheet 12 to hold the diaper in place after applying the diaper to the infant.

In FIG. 2, there is shown a diaper 27 having a shaped absorbent batt 28 and an opening 32 in the liquid barrier 30. A covering 34 is located beneath the opening and is comprised of a moisture-permeable substance. At one end of the diaper along both longitudinal side margins are a pair of adhesive tape tabs 36 for affixing the diaper about the infant. The absorbent batt 28 has two parallel end margins and two parallel longitudinal side margins. Disposed along each longitudinal side portion is an indentation with the indentations opposite each other. The indentations have a quarter circle front portion and a uniformly sloped back portion and are positioned approximately one-third of the distance along the length of the batt.

In the embodiment of FIG. 3, there is shown a diaper 39 having an absorbent batt 40, a liquid barrier 42 with an opening 44 in the liquid barrier 42 and a moisture-pervious covering 46 located beneath the opening. Elastic ribbons 50 are affixed in the longitudinal side margins in the central region to improve the fit of the diaper about the infant's legs. Adhesive tape tabs 48 are used to affix the diaper about the infant.

FIG. 4 illustrates the configuration of the diaper 60 after being put on an infant. The diaper is fastened with tape tabs 68. Each tape tab has a fixed end secured to the diaper and a free end having an adhesive surface on one side covered with a facing sheet. The facing sheet is removed to expose the adhesive surfaces when the diaper is applied to the infant and the free end of the adhesive tab is secured to the corner of the diaper. The opening 66 is located in the liquid barrier 62 so as to cover most of the perineal region. If desired, more than one set of tapes may be provided for refastening the diaper after removal.

FIG. 5 depicts another embodiment of the present invention of a diaper 70 comprised of a backing sheet 72, an absorbent batt 74, a liquid barrier 76 and a facing cover 78. The liquid barrier 76 has an opeing 80 which is covered by the facing cover 78. The facing cover is a moisture-pervious substance which is not water wettable but presents a smooth surface to the skin. Embossed lines 82 are impressed on the diaper and adhesive tape tabs 84 are affixed to the diaper to hold it in place after applying the diaper to the infant.

FIG. 6 illustrates a disposable training panty. The baby training panty 101 is preferably constructed from a light-weight, non-woven fabric formed predominantly of short-length cellulosic fibers with a minor percentage of long fibers in a non-woven web of the type disclosed in U.S. Pat. No. 3,663,348 to Liloia et al. Other non-woven webs that can be used are the so-called transition webs manufactured by the process disclosed in U.S. Pat. No. 3,768,118 to Ruffo et al. Other suitable webs are carded or spun-bonded long-fiber non-woven webs such as those disclosed in U.S. Pat. No. 3,815,602. It is preferred that thermoplastic fibers be included in the webs, so that the undergarment may be assembled by heat sealing techniques.

Prior be being cut into a blank suitable for use in the construction of the baby panty of this invention, the non-woven web can be made stretchable by compressive shrinking preferably by compacting the fabric in the cross direction and micropleating in the machine direction, so that the extensibility to rupture preferably is at least about 30 percent, and more preferably greater than about 55 percent, in the machine direction, and preferably at least about 40 percent, and more preferably greater than about 60 percent, in the cross direction. Such a fabric will be hereinafter referred to as a compressively-shrunk fabric.

The baby training panty 101 is a multi-layered construction having a front portion 102, a rear portion 103, a crotch portion 104, a front waistband section 105 and a rear waistband section 106 which together form a self-fitting waistband, side seams 107 and 108, and self-fitting leg apertures 109 and 110. Side seams 107 and 108 are secured by securement lines such as glue lines 111 and 113, respectively. The opening 114 in the training panty is located in the liquid barrier 115 so as to cover most of the perineal region. As in the case of the diaper described heretofore, the opening 14 may permit immediate contact with the internal absorbent batt or the area beneath the opening may be covered by a moisture-pervious covering.

Figure 7:
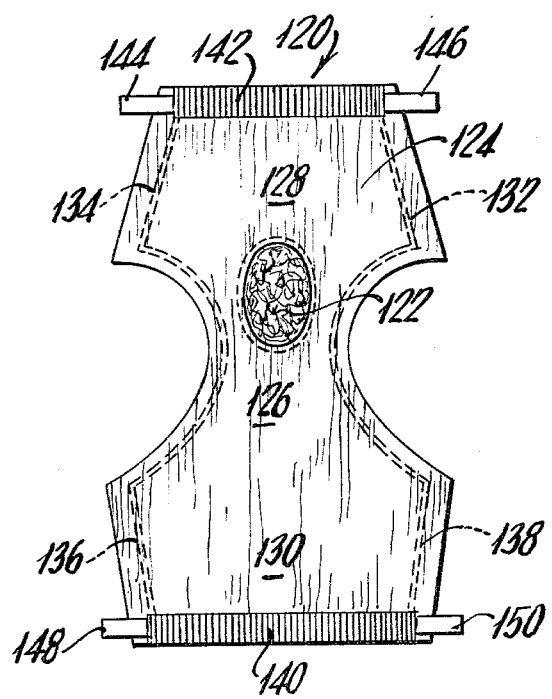
FIG. 7 is a plan view of an assembled training panty of FIG. 6 wherein the sides have not been seamed and FIG. 8 is a perspective view with certain portions broken away for clarity of illustration of one embodiment of a diaper of the present invention.

FIG. 7 illustrates the training panty of FIG. 6 in plan view. The training panty 120 is assembled except for the side seams. The opening 122 in the liquid barrier 124 is placed in the central region 126 nearer the front panel 128 than the rear panel 130. In this embodiment the liquid barrier is adhered to the moisture-impermeable backing sheet by glue lines 132, 134, 136, and 138. Elastic strips are pre-stretched and secured to the end portions to form a gathered rear waistband section 140 and a gathered front waistband section 142. The ends, 144, 146, 148, and 150 of the elastic strips, are usually cut off when the final assembly is carried out.

Figure 8:
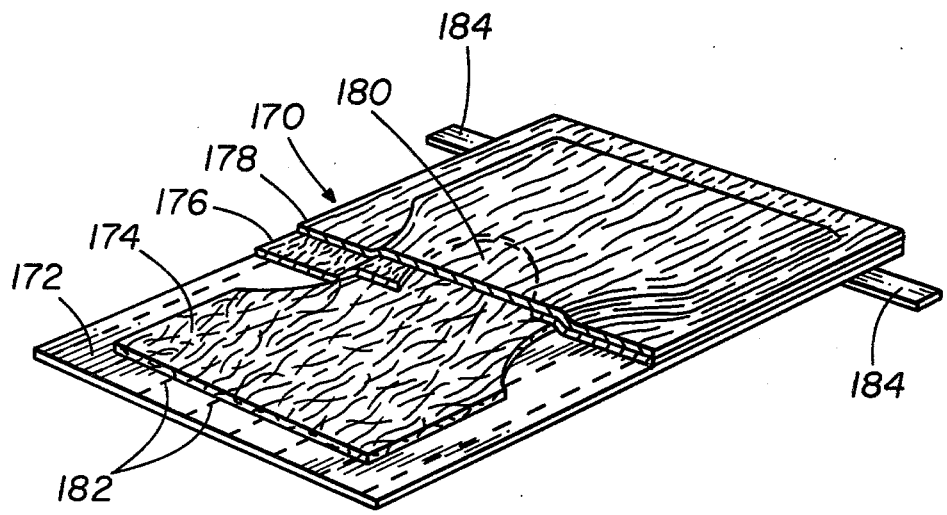

FIG. 8 depicts another embodiment of the present invention of a diaper 170 comprised of a backing sheet 172, an absorbent batt 174 of hourglass shape, a liquid barrier 186 and a facing cover 178. The liquid barrier 176 has an opening 180 which is covered by the facing cover 178. The facing cover is a moisture-pervious substance which is not water wettable but presents a smooth surface to the skin. Embossed lines 82 are impressed on the diaper and adhesive tabs 84 are affixed to the diaper to hold it in place after applying the diaper to the infant.

In a preferred embodiment of the invention, the moisture-impervious sheet is formed of polyethylene having a thickness of approximately 0.001 inch. The sheet may be smooth, micropleated, or may be embossed to improve its drape and feel. Other suitable flexible moisture-impervious sheets may be used in accordance with the invention, such as, for example, polyethylene terephthalate sheets having a thickness of about 0.0005 inch.

The absorbent batt preferably is formed of loosely compacted short cellulose fibers, such as wood pulp fibers, or cotton linters, or mixtures thereof, which primarily are held together by interfiber bonds requiring no added adhesive, as is known in the art. Briefly, these batts are a low bulk density coherent web of loosely compacted cellulose fibers, preferably comminuted wood pulp fibers, in the form of so-called "fluff".

The term "short fibers", as used herein, refers to fibers less than about ¼ inch in length, in contrast to "long fibers", or "textile length fibers" which are longer than about ¼ inch in length, and generally are between about ½ and 2½ inches in length.

Preferably the absorbent batt includes a paper-like, densified compacted cellulosic fibrous layer of relatively high wettability and relatively high fluid retentivity integral with the batt on the side thereof in contact with the backing sheet. The paper-like densified layer is formed by slight moistening of one surface of the batt followed by the application of pressure thereto. This densified skin portion provides a wickability gradient to draw urine from the more loosely compacted cellulosic fibrous layer into the densified layer. The densified skin portion is described in more detail in Burgeni U.S. Pat. No. 3,017,304.

The composite density of the absorbent batt should be above about 0.07 gm/cc and preferably between about 0.10 and 0.15 gm/cc. The foregoing density values are applicable to the diaper as produced. In storage and handling, the loft or thickness of the batt is increased to some extent, resulting in lower densities.

The liquid barrier is any liquid barrier material that is soft and flexible as well as non-noisy. Although it need not be, it is preferable that the liquid barrier material be "breathable". For example, the material may be a plastic film, a repellent-treated wet strength tissue, a repellent wet-laid non-woven fabric or a repellent dry-laid non-woven fabric. Specifically, the liquid barrier material may be a non-woven web made up of a mixture of fibers consisting predominantly of short cellulosic fibers such as wood pulp fibers or cotton linters. The short fibers are in uniform admixture with 2 to 25% by weight of textile length fibers, such as rayon fibers uniformly cut to 1½ inches in length. The short and long fibers are randomly and substantially uniformly dispersed and bonded with a bonding agent such as a self-crosslinking acrylic emulsion. This web is then treated with a water-repellent agent to impart moisture-repellent characteristics to the liquid barrier material.

In another example the liquid barrier material is the same material as used in the backing sheet, e.g. a polyethylene film material. In this case the liquid barrier and the backing sheet can be heat sealed in the margins thus eliminating the necessity for gluing one to the other.

The opening in the liquid barrier is situated so as to cover the perineal region of the wearer when the diaper is applied. Preferably the opening is closer to one short side of the batt than the other to define a short front portion of the batt and a longer rear portion of the batt. The opening in the instance of the most preferred embodiment is placed about one-third of the length of the batt from the short side defining the front portion.

Although it is not necessary to include a covering beneath the opening in the liquid barrier material, it is preferable to do so to prevent wadding or linting of the absorbent batt after the absorbent batt is subjected to the urine. This covering material preferably is a mixture of fibers consisting predominantly of the short cellulosic fibers described above but including from about 2% to about 25% by weight of textile length fibers. The covering material is treated with a wetting agent to permit penetration by liquid through the covering material to the absorbent batt. The covering may be placed beneath the opening upon the absorbent batt. Alternatively the covering may be placed above the opening and secured to the liquid barrier. In each instance the covering is of a size sufficient to cover the opening and is adhered to the liquid barrier or the absorbent batt so as to remain in a fixed position.

In another embodiment of the present invention (FIGS. 5 and 7) when the liquid barrier is a polyethylene film material, it may be desirable to place a fibrous facing layer over the polyethylene layer so that the facing layer is between the infant and the liquid barrier layer. When utilizing such a facing layer it is not necessary to include a covering beneath the opening in the liquid barrier. The facing layer preferably is unwettable but is moisture-pervious. It, generally, is soft to present a smooth surface to the skin.

The body of the absorbent batt tends to draw liquid away from the covering layer. The individual fibers of the batt are extremely wettable, generally having liquid-fiber contact angles below about 15° and approaching 0 in the optimum embodiment. The wickability, or preferential absorptivity, of the body of the batt for water is limited, however, by its low density which results in a large effective capillary radius for the capillaries between adjacent fibers. The pressure causing a liquid to enter a cylindrical capillary is expressed by the equation:

$$P = (2\gamma \cos \theta / r)$$

P is the capillary pressure,
$\gamma$ is the surface tension of the liquid,
$\theta$ is the liquid-fiber contact angle, and
r is the capillary radius With a given liquid, the pressure (capillary force) increases with the cosine of the liquid-fiber contact angle (reaching a maximum where the angle is 0), and increases with narrower capillary radii so that narrower capillaries will draw liquid from wider ones.

The relative wickability between the covering layer, or if present, the facing layer, and the body of the batt is affected by both the relative densities of the layers and the relative wettability of the individual fibers of each layer. The facing layer or covering layer is sometimes more dense than the body of the batt, tending to provide greater wickability in the covering layer or facing layer, but even then the individual fibers of the batt have substantially smaller liquid-fiber contact angles than those of the facing layer, overcoming the density difference and providing a substantial overall increase in capillary pressure to absorb liquid into the body of the absorbent batt.

The densified fiber layer of the absorbent batt provides the maximum capillary pressure because it combines the very low contact angle of the fibers of the absorbent batt with the high density (small capillary radius) of the densified fibers in the densified layer. Thus, the densified layer provides a wickability gradient for drawing urine from the absorbent batt into the densified fiber layer.

When the urine passes through the opening and through a covering layer, if one is present, it comes into contact with the body of the batt and spreads within the body of the batt to wet a larger roughly circular zone therein. The urine is then strongly drawn to the high density of the densified layer and is spread laterally through a much larger substantially circular zone or to the edges of the densified layer depending on the amount of the urine passed.

On occasion when a substantial amount of urine has been voided, the densified layer becomes saturated and excess urine, aided by the presence of the moisture-impervious backing sheet and its adherence to the densified layer in a discontinuous pattern substantially throughout the interface therebetween, flows into the previously dry portions of the batt. The liquid barrier material provides a barrier which traps the urine in the batt to insure that the side of the liquid barrier material facing the infant remains dry.

There is also cooperation between the densified layer of the absorbent batt and the moisture-impervious backing sheet to which it preferably is adhered. A voiding of urine usually takes place within a short time, and the rate of absorption of the diaper might be overwhelmed during this short period in spite of the diaper's ultimate capacity to absorb the amount of liquid voided and in spite of the relatively high rate of absorption obtainable for the reason specified above. The moisture-impervious backing sheet serves to hold the urine and keep it from wetting the bedclothes or outer clothing so that the absorptive portions of the diaper can have the time to function. In addition, the impervious backing sheet serves as an anchor to stabilize the fluff portion of the batt against migration of the loosely compacted fibers.

The opening in the liquid barrier is generally from about 15% to about 30% of the length of the absorbent batt and from about 15% to about 30% of the width of the absorbent batt. Preferably the opening is from about 15% to about 20% of the width and length of the absorbent batt. The opening may be rectangular in shape or oval or any other suitable shape, preferably the opening is oval.

Suitable fibrous structures for making the absorbent batt used in the present invention are made from short cellulosic fibers obtained by the grinding or comminution of compacted wood pulp fibers or cotton linters. The compacted cellulosic material is at a moisture content of 5–10% by weight (or is slightly moistened to bring it to that range) before being subjected to the grinding operation so that the fibers produced by grinding have sufficient moisture to have the capability of developing weak interfiber hydrogen bonds which give some coherence to the body of the absorbent batt. The batts are initially formed by air blowing the slightly moist cellulosic fibers onto a support at a total weight of about 2 to about 10 oz/yd$^2$, and then subjecting the air blown fibers to heavy compression. The small amount of moisture which, when required, may be added to cellulosic pulp board is uniformly distributed throughout the air blown fibers by the grinding and air blowing operations and, after compression, this moisture provides weak hydrogen bonding to give some integrity to the body of the batt.

The short fibers used in making the absorbent batt of the present invention are generally entirely fibers of wood pulp or cotton linters. However, other cellulosic fibers may be used as well as blends of cellulose fibers with other fibers such as silk, wool, nylon, rayon or cellulose acetate, or peat moss and the like. Optionally superabsorbents may be added to the fibrous structure of the absorbent batt.

Several different types of materials can be used for the covering layer, or if desired, the facing layer. These materials may be made of an apertured, non-woven fabric which is found, for example, in accordance with the teachings of commonly assigned U.S. Pat. Nos. 2,862,251; 3,081,514 and 3,081,515. Other fabrics which are moisture-pervious but substantially unwettable are also suitable.

When preparing a diaper or training panty in accordance with the present invention, it is preferred to adhere the impervious backing sheet to the densified layer of the absorbent batt, continuously or discontinuously, over substantially the entire interface between them so as to prevent substantial separation between the two resulting in the creation of spaces in which substantial amounts of free liquid urine can accumulate. The adherence of the impervious backing sheet to the paper-like densified cellulosic layer effects a dimensional stabilization of the densified layer against transverse movement and thereby brings about a stabilization of the loosely compacted fiber fluff portion of the absorbent batt since the paper-like densified layer is integral with the fluff portion. In addition holding forces are transmitted from the dimensionally stable impervious backing sheet through the widely distributed adhesive, to the densified layer, and thence to the fluff. Thus when using a stabilized absorbent batt it may not be necessary to provide either a covering or a facing layer over the opening in the liquid barrier of the diaper of the present invention.

I claim:

1. A disposable diaper comprising a first outer layer in the form of a moisture-impervious backing sheet; an absorbent batt positioned in superposed relationship with respect to the backing sheet, the batt being smaller than the backing sheet and spaced inwardly from the longitudinal sides thereof; and a second outer layer in the form of a liquid barrier positioned in superposed relationship with respect to the batt on the side opposite the backing sheet, the liquid barrier being larger than the batt and substantially coterminous with the backing sheet and having longitudinal side margins thereof secured to the backing sheet and having a single opening situated so as to contact the perineal region of the wearer, the opening and the liquid barrier being covered by a facing layer on the side opposite the batt.

2. A disposable diaper as in claim 1 wherein the opening is oval shaped and closer to one short side of the batt than the other to define a short front portion of the batt and a longer rear portion of the batt.

3. A disposable diaper as in claim 1 wherein a shaped absorbent batt is provided having an indentation in each long side, said indentations being disposed opposite each other.

4. A disposable diaper as in claim 3 wherein the indentations are closer to one short side of the batt than the other to define a short front portion of the batt and a longer rear portion of the batt to provide an improved fit.

5. A disposable diaper as in claim 3 wherein the absorbent batt is hourglass in shape.

6. A disposable diaper as in claim 1 wherein an elongated, inherently elastic ribbon member is disposed along each longitudinal side margin of said diaper and secured thereto providing an elastic region in the central area to effect an improved fit.

7. A disposable diaper comprising a first outer layer in the form of a moisture-impervious backing sheet; an absorbent batt positioned in superposed relationship with respect to the backing sheet, the batt being smaller than the backing sheet and spaced inwardly from the longitudinal sides thereof; and a second outer layer in the form of a liquid barrier positioned in superposed relationship with respect to the batt on the side opposite the backing sheet, the liquid barrier being larger than the batt and substantially coterminous with the backing sheet, and having longitudinal side margins thereof secured to the backing sheet, and having a single opening situated so as to contact the perineal region of the wearer; the opening being in length from about 15% to about 30% of the longitudinal length of the absorbent batt, the opening and liquid barrier being covered by a facing layer on the side opposite the batt.

8. A disposable diaper comprising a first outer layer in the form of a moisture-impervious backing sheet; an absorbent batt positioned in superposed relationship with respect to the backing sheet, the batt being smaller than the backing sheet and spaced inwardly from the longitudinal sides thereof and being substantially hourglass in shape by having an indentation along each parallel side opposite each other and having a paper-like, densified, compacted, cellulosic fibrous layer of relatively high wettability and relatively high fluid retentivity integral with the batt on the surface thereof in contact with the backing sheet; and a second outer layer in the form of a liquid barrier positioned in superposed relationship with respect to the batt on the side opposite the backing sheet, the liquid barrier being larger than the batt and substantially coterminous with the backing sheet, and having a longitudinal side margin thereof secured to the backing sheet, and having a single oval-shaped opening situated so as to contact the perineal region of the wearer, the opening being in length from about 15% to about 30% of the longitudinal length of the absorbent batt, the opening and the liquid barrier being covered by a facing layer on the side opposite the batt.

* * * * *